(12) United States Patent
Sgarlato (10) Patent No.: US 7,338,765 B2
(45) Date of Patent: Mar. 4, 2008

(54) REPRESENTATIONAL FRAGMENT AMPLIFICATION

(75) Inventor: Gregory D. Sgarlato, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/221,490

(22) Filed: Sep. 7, 2005

(65) Prior Publication Data

US 2006/0051801 A1  Mar. 9, 2006

Related U.S. Application Data

(60) Provisional application No. 60/607,910, filed on Sep. 7, 2004.

(51) Int. Cl.
*C12Q 1/68* (2006.01)
*C12P 19/34* (2006.01)

(52) U.S. Cl. .................. 435/6; 435/91.1; 435/91.2
(58) Field of Classification Search ............. None
See application file for complete search history.

(56) References Cited

U.S. PATENT DOCUMENTS

| | | | |
|---|---|---|---|
| 6,017,701 A | 1/2000 | Sorge et al. | |
| 6,270,966 B1* | 8/2001 | Weinstein et al. | 435/6 |
| 6,280,948 B1 | 8/2001 | Guilfoyle et al. | |
| 6,291,170 B1 | 9/2001 | Van Gelder | |
| 2003/0027141 A1* | 2/2003 | MacLeod et al. | 435/6 |
| 2003/0039992 A1* | 2/2003 | Chakrabarti et al. | 435/6 |

OTHER PUBLICATIONS

Hubank et al., Identifying differences in nRNA expression b y representational difference analysis of cDNA, (1994), N.A.R., 22:5640-5468.
Lisitsyn et al., Cloning the differences between two complex genomes, (1993), Science, 259:946-951.
Ramsay, DNA chips: state-of-the-art, (1998), Nat. Biotech., 16:40-44.
Seth et al., SMART amplification maintains representation of relative gene expression: quantitative validation by real time PCR and application to studies of alcoholic liver disease in primates, (2003), J Biochem Biophys Methods, 55(1):53-66.
Smith et al., Single primer amplification (SPA) of cDNA for microarray expression analysis, (2003), Nucleic Acids Res., 31(3):e9.
Walker et al., Isothermal in vitro amplification of DNA by a restriction enzyme/DNA polymerase system (1992), P.N.A.S., 89(1):392-6.

* cited by examiner

*Primary Examiner*—Young J. Kim
*Assistant Examiner*—David C. Thomas
(74) *Attorney, Agent, or Firm*—Bozicevic, Field & Francis LLP; Pamela J. Sherwood (57) ABSTRACT

Methods and kits are provided for non-preferential amplification of a population of nucleic acids. The methods allow for a high degree of amplification, where representation in the final population has a direct linear relationship with the starting material. The amplification product is useful as a probe for hybridization; for generation of libraries, for sequencing, and the like.

6 Claims, 7 Drawing Sheets

FIGURE 1
Schematic of RFA

Pooling of amplified NlaIII and DpnII-linkered cDNA generates RFA amplicon which includes 3' end of transcripts.

Pooled double-stranded RFA is biotin-labeled by 8-mer Klenow amplification and hybridized to microarrays.

FIGURE 2

Fold amplification: Determination of copy numbers present in total amplicon generated from 1 ul cDNA

FIGURE 3

Fragments with varying GC content amplify with varying efficiency

Example: ZWINT DpnII fragment vs NlaIII fragment

Gatctctctcagttgtgtatttgttcatcttcatatgctggcaggaacaactattaatacagatactcagaagccaataacatg
acaggagctgggactggtttgaacacaggglglgcagatggggaggggglactggccttgggcctcctatgatgcaga
catggtgaatttaattcaaggaggaggagaatgttttaggcaggtggttatatgtgggaagataattttattcatggatc DpnII fragment length: 242 nt (includes NlaIII fragment)
DpnII GC content: 44%
Fold amplification: ~80,000- 120,000 (VNM277) ◄—— Efficient amplification catgacaggagctgggactggtttgaacacaggglglgcagatggggaggggglactggccttgggcctcctatgatgcagacatg

NlaIII fragment length: 86 nt
NlaIII GC content: 58%
Fold amplification: ~4,000-17,000 (VNM277) ◄—— Less efficient amplification

TaqMan primer sites     Restriction enzyme recognition sites

FIGURE 4

9 | Single Gene, Detailed Analysis:Cyclin B1 (NM 031966)

FIGURE 5

Intensity of Match vs Mismatch for Disease and Normal from VNM285 HG-U133A:214710_s (CCNB1)

11 probes of 214710_s on HG-U133A listed on the x axis, intensity on the z axis.
Note: signal intensity not to scale for comparison of hybridization pattern.

FIGURE 6

RFA Disease/Normal ratio summary

| Patient | CCNB1 | SPINT2 | ZWINT |
|---|---|---|---|
| *Taqman analysis:* | | | |
| VNM277 DpnII amplicon | 1.04 | 1.39 | 1.06 |
| VNM277 NlaIII amplicon | 0.99 | 0.98 | 1.03 |
| VNM277 cDNA | 1.28 | 1.43 | ND |
| *Microarray HG-U133A:* | | | |
| VNM277 DpnII-NlaIII RFA | 1.40 | 1.20 | 2.10 |
| | | | |
| *Taqman analysis:* | | | |
| VNM285 Dpn Taqman | 3.38 | 2.96 | 3.12 |
| VNM285 Nla Taqman | 4.63 | 2.65 | 2.42 |
| VNM285 cDNA Taqman | 3.80 | 2.46 | ND |
| *Microarray HG-U133A:* | | | |
| VNM285 DpnII-NlaIII RFA | 8.50 | 3.60 | 6.21 |

FIGURE 7

Disease and Normal Match Corrected Intensity to Scale VNM285 HG-U133A:214710_s (CCNB1)

| | 1 | 2 | 3 | 4 | 5 | 6 | 7 | 8 | 9 | 10 | 11 |
|---|---|---|---|---|---|---|---|---|---|---|---|
| n corrected | 50.8 | 794.8 | 41.2 | 242 | 1159.5 | 917.3 | 21.7 | 96 | 198 | 282 | -37 |
| d corrected | 468.7 | 5330.5 | 552.3 | 1605.8 | 3642.8 | 3314 | 474 | 699 | 2200.2 | 1926.5 | -29.5 |

Corrected d and n Intensiy Data =(Match - Mismatch)
CCNB1 is confirmed to be 3.4 fold upregulated in Patient VNM285 by Real-time Quantitative PCR anlysis (data not shown)

REPRESENTATIONAL FRAGMENT AMPLIFICATION

BACKGROUND OF THE INVENTION

In many important areas of research, particularly those involving complex biological systems, obtaining sufficient mRNA for expression analysis, alternative splicing and SNP variation is problematic. Limiting factors include the high complexity of the mRNA, the relatively low abundance of many important expressed messages, and the spatially limited expression of these messages.

A tool showing considerable promise for genetic analysis is the nucleic acid array, reviewed by Ramsay (1998) Nat. Biotech. 16:40-44. These arrays contain dense collections of nucleic acids, either PCR products or oligonucleotides, usually of known sequence, that have been either synthesized or printed at fixed spatial locations on suitable substrates, such as nylon filters or glass slides. When labeled DNA or RNA samples are hybridized to the arrays, the abundance of specific sequences in solution can be quantitated based on the fluorescent or radioactive signal intensity at the position of the complementary probe. However, the substantial amounts of labeled probes required, for example to hybridize to microarrays, makes it difficult to test small tissue samples and groups of isolated cells in such methods.

While amplification methods have been previously described, such methods suffer from a skewing of representation, where the end product does not reflect the distribution of species in the starting population. Prior art methods include T7 transcription of cDNA, as described by Van Gelder et al., U.S. Pat. No. 6,291,170; tissue culture of cells to increase the absolute quantity of RNA harvest; single primer isothermal amplification (Walker et al. (1992) P.N.A.S. 89(1):392-6); SMART cDNA amplification (Seth et al. (2003) J Biochem Biophys Methods. 55(1):53-66); single primer amplification (SPA) over a 40 cycle asymmetric amplification (Smith et al. (2003) Nucleic Acids Res. 31 (3):e9).

Lisitsyn et al. (1993) Science 259:946-951) introduced a PCR-based method referred to as representational difference analysis (RDA). RDA utilizes PCR to enrich for unique species in one of the samples after hybridization and polymerization steps. RDA uses two separate ligations of two different adaptors to enrich for unique species. After an initial PCR amplification of both tester and driver samples with a first adaptor, a second adaptor is attached to the ends of tester DNA but not the driver DNA. Then, after mixing the second adaptor-treated tester DNA with driver DNA, denaturing, hybridizing, and filling in overhanging ends, only double stranded tester DNA should amplify exponentially with PCR primers specific for the second adaptor sequences. The tester:driver hybrids should amplify linearly and the driver:driver hybrids should not amplify at all.

In order to be effective for cloning, RDA requires a reduced complexity in the starting material used. To reduce the complexity, RDA generally employs a digestion of total genomic DNA with a six base pair-cutting enzyme and amplifying the digested DNA by PCR. A high proportion of the digested fragments do not fall within the amplifiable range of 150-1000 base pairs. Larger fragments are not amplified, reducing the complexity of the amplicon so that the final representation contains only about 2-10% of the total genome. Of course, the representations of the PCR will not encompass the entire sequence information available in the genome. Consequently, desired sequences may not be represented in the subtracted library while undesired species may be represented in the subtracted library.

RDA was been applied to cDNA subtraction by Hubank and Schatz (1994) N.A.R. 22:5640-5648. The method is very similar to RDA described by Lisitsyn et al., with cDNA being used as the starting material instead of genomic DNA. As with RDA, there are two adaptor ligation steps. The method is designed so that only tester:tester hybrids contain the PCR primer binding sites on both ends of the strands of DNA, and thus are the only species that are exponentially amplified. In contrast to the complexity of genomic RDA, a population of cDNA derives from some 15,000different genes in a typical cell and represents only about 1-2% of the total genome. Therefore, RDA can apparently be applied to cDNA without the need to first reduce the complexity.

The hybridization goes to completion which allows the selection of rare sequences in the tester population. The more abundant driver population competes out the tester population through hybridization, which results in non-exponential products. Consequently, the more abundant nucleic acids in the tester population will have a higher probability of subsequent exponential amplification than the rare nucleic acids. The linearly amplified rare nucleic acids can effectively become lost from the amplified population.

There remains a need in the art for new and improved methods to amplify populations of nucleic acids, particularly mRNA populations, where there is a significant increase in the amount of testable material, with direct linear relationship to the starting population. By providing methods for non-preferentially replicating or amplifying nucleic acids, the disclosed invention fulfills those needs. The ability of this divergent population of molecules to be amplified efficiently provides a means of generating probes and libraries of expression signatures; and consequent insights into the biology of living systems.

SUMMARY OF THE INVENTION

Methods and kits are provided for non-preferential amplification of a population of nucleic acids. The methods allow for a high degree of amplification, where representation in the final population has a direct linear relationship with the starting material, when two populations are compared. Starting material may include chromosomal DNA, extrachromosomal DNA; and/or various RNA populations, including the mRNA expression product of a cell, tissue or organism. The ability to amplify signal from very low concentrations of starting material allows the testing of a wide variety of cell populations and conditions. All expression information will be available for analysis, including relative expression levels, SNP information, and alternative splicing information. After amplification the product can be labeled with a detectable label, e.g. fluorescent, biotinylated derivatives, and the like. The amplification product is useful as a probe for hybridization; for generation of libraries, for sequencing, and the like.

The procedure for representational fragment amplification (RFA) comprises an initial synthesis of cDNA, utilizing an oligo dT primer that has been modified to comprise restriction sites for one or more frequent cutter restriction enzymes. No modifications are needed for chromosomal DNA, but there is no primer needed and the amount of starting DNA is higher due to the requirement of at least 2-5 copies of every fragment in the genome. The DNA strand complementary to the cDNA is synthesized, and optionally, when a complete cDNA sequence is desired, linkers comprising restriction sites for the same one or more frequent cutter restriction enzymes are ligated to the 5' end of the double stranded cDNA. The product of the ligation is then digested with the one of the cognate one or more frequent cutter restriction enzyme(s). Where two or more restriction sites have been provided in the linkers, the reaction may be split, and separately digested with each of the cognate enzymes. The resulting digestion may be pooled for amplification, or separately amplified. Non-phosphorylated linkers are ligated to the fragments of the restriction digestion. 5' to 3' linker pairs are usually hybridized to generate a complementary overhang prior to ligation.

The linkered fragments are then exponentially amplified by PCR, e.g. with a single primer complementary to the sites established with the preceding primer ligation. The amplified product thus obtained provides an accurate representation of the original population, but in a significantly greater quantity.

BRIEF DESCRIPTION OF THE DRAWINGS

FIG. 2 illustrates the determination of copy number present in total amplicon generated from a microliter of cDNA. Fold amplification calculations: Fold amplification values as determined by copy number were calculated by multiplying average copy numbers from known dilutions of template by appropriate dilution factors to determine the equivalent number of copies present in 1 μl cDNA, and dividing the resulting amplicon copy numbers by the resulting cDNA copy numbers. An example follows: 1.73 μl of VNM277 normal cDNA was digested with either DpnII or NlaIII and ligated to appropriate linkers in a total volume of 106 μl. This results in 0.016 μl cDNA/μl digest-ligation reaction, or a dilution factor of 61.0. 0.5 μl of the NlaII digest-ligation reaction was used as template in an amplification reaction. This 0.5 μl of digest-ligation corresponds to (0.5 μl digest-ligation reaction×0.016 μl cDNA/μl digest-ligation reaction=0.008 μl) of cDNA. The resulting 100 μl of amplicon had a concentration of 240 ng/μl. One microliter of amplicon was diluted to 5 ng/μl in tRNA buffer, a dilution factor of 48.0. The 5 ng/μl dilution was then diluted another 100-fold for use as template in the TaqMan reaction. 1.5 μl was used as template. The starting cDNA was diluted 1/50 for use as template. 1.5 μl was used as template. Calculation back: Average copy numbers for both cDNA and amplicon templates were divided by 1.5. The average copy number for a gene for the NlaIII amplicon template was then multiplied:—by 4800 to get to the number of copies in 1 μl undiluted amplicon (100 to get up to the copies in 5 ng/μl, and 48 to get up to the copies in 1 μl undiluted amplicon);— by 100 to get to the number of copies in all 100 μl of amplicon;—by 2 to get to the number of copies that would have been present if 1 μl of the digest-ligation reaction had been used;—by 61 to get to the number of copies that would have been present if 61 μl of the digest-ligation reaction (equivalent to 1 μl of cDNA) had been used for amplification. The average copy number for a gene for the cDNA was multiplied by 50 to get the number of copies that would be present in 1 μl cDNA. Fold amplification: Amplicon copies from 1 μl cDNA/cDNA copies from 1 μl cDNA.

DETAILED DESCRIPTION OF THE EMBODIMENTS

Methods are provided for non-preferential amplification of a population of nucleic acids. The methods allow for a high degree of amplification, where representation in the final population has a direct linear relationship with the starting material. The starting material may be amplified about $10^3$-fold; about $10^4$-fold, or more. The representation of species will generally vary by not more than 50% between the starting material and the amplified product; and may vary less than about 25%, or less.

Essentially any nucleic acid sequence, in purified or nonpurified form, can be utilized as the starting nucleic acid(s) for the methods of the present invention, provided it contains or is suspected to contain the specific nucleic acid sequences of interest. A mixture of any of these nucleic acids may also be employed. It is not necessary that the sequence to be amplified be present initially in a pure form. The nucleic acid(s) may be obtained from any source, for example from natural DNA or RNA from any source, including bacteria, yeast, viruses, organelles, and higher organisms such as plants or animals. DNA or RNA may be extracted from blood, tissue material or cells by a variety of techniques known in the art.

In one general embodiment of the present invention, cDNA strands are synthesized from a collection of mRNAs using a complex oligonucleotide primer. The procedure for representational fragment amplification (RFA) comprises an initial synthesis of cDNA, utilizing an oligo dT primer that has been modified to comprise restriction sites for one or more frequent cutter restriction enzymes. The primer will generally comprise two regions, a region of poly-dT sequence, usually of at least about 8 residues, more usually at least about 12 residues, and may be at least about 18 residues or longer, as is known in the art. Flanking the dT region on the 5' end is an oligonucleotide providing at least one site for a frequent cutter restriction enzyme. Such restriction enzymes are known in the art, and may include sites for enzymes that recognize common 4 bp sequences, e.g. DpnII (GATC) (also known as NlaII), NlaIII (CATG) etc. The methods may be practiced with an oligonucleotide that comprises one, two, three or more restriction sites, where such sites may be overlapping or non-overlapping. The use of two or more sites allows parallel processing with each of the cognate enzymes, and reduces the possibility of sequences being lost.

The oligonucleotide primers may be prepared using any suitable method, such as, for example, the well known phosphotriester and phosphodiester methods, or automated embodiments thereof. In one such automated embodiment, diethylphosphoramidites are used as starting materials and may be synthesized as described by Beaucage et al., Tetrahedron Letters 22: 1359-1962 (1981).

Once the primer hybridizes to the mRNA, a first cDNA strand is synthesized. This first strand of cDNA is preferably produced through the process of reverse transcription, wherein DNA is made from RNA, utilizing reverse transcriptase following standard techniques. This enzyme, present in all retroviruses, e.g., avian myeloblastoma virus, adds deoxyribonucleotides to the 3' terminus of the primer.

The second strand cDNA, creating double-stranded (ds) DNA, can be synthesized by a variety of means, but preferably with the addition of RNase H and E. coli DNA polymerase. RNase assists breaking the RNA/first strand cDNA hybrid, and DNA polymerase synthesizes a complementary DNA strand from the template DNA strand. The second strand is generated as deoxynucleotides are added to the 3' terminus of the growing strand. As the growing strand reaches the 5' terminus of the first strand DNA, the complementary promoter region of the first strand will be copied into the double stranded promoter sequence in the desired orientation. After the DNA strand complementary to the cDNA is synthesized, linkers comprising restriction sites for the same one or more frequent cutter restriction enzymes are ligated to the 5' end of the double stranded DNA. The linkers are double stranded and generally follow the constraints described above for the restriction enzyme recognition sequence(s). An alternate method of attaching 5' restriction sites uses a template switching logo that contains the restriction site for one or more 4 base restriction enzyme recognition sequences, for example, Oligo Dpn/NlaTempSwitcher 5' GAGAGTGAGTGATCATGGGG 3' (SEQ ID NO:19) Both linker and template switching primers are optional when working with commercial expression arrays because most are designed to work with 3' bias probe generation, like the T7 RNA synthesis system.

The product of the ligation is then digested with the cognate restriction enzyme. Where two or more restriction sites have been provided in the linkers, the reaction may be split, and separately digested with each of the enzymes. The reaction is usually allowed to proceed to completion. Non-phosphorylated linkers are ligated to the fragments of the restriction digestion to provide suitable sites, as shown in the examples.

The linkered fragments are then exponentially amplified by PCR, e.g. with a single primer complementary to the sites established with the preceding primer ligation. The amplification reaction is performed for at least about 15 cycles, usually at least about 20 cycles, and may be performed for about 25 cycles, about 30 cycles, or more. As used in this invention, "amplifying" means adding the appropriate reagents (i.e. primers with appropriate sequences, enzymes, polymerases, nucleotides, buffers, etc.) to a sample in order to reproduce, generally in a sequential fashion, numerous copies of one or more nucleic acids present. One skilled in the art is familiar with various nucleic acid amplification reactions, such as the polymerase chain reaction resulting in amplified DNA. Various modifications of the basic amplification reactions, as known in the art, can also be employed with specific embodiments of this invention. The nature of the amplification reaction selected depends on various factors such as the original source of nucleic acids and the desired final products. There is, therefore, no limitation to the type of amplification reaction that can be employed during the "amplifying" step in the methods of this invention. The conditions used for "amplifying" will vary with the type of reaction selected.

The amplified product is used in various methods known in the art. Where the product is used as a probe, it may be labeled with a detectable marker, e.g. fluorescein or biotin labeled nucleotide derivatives are incorporated by reaction with polymerase. Nucleotides may be obtained which are labeled with biotin, where these nucleotides will become incorporated in the product. The biotin may then be used for binding to avidin, which is labeled with an appropriate label capable of providing for detection. A wide variety of labeling techniques are well known to those skilled in the art and may be used in accordance with standard procedures (see, U.S. Pat. No. 4,755,619, which is incorporated herein by reference). Alternatively the probes may be labeled by end-labeling; etc.

In some embodiments of the invention, a G+C enhancing agent is included in the amplification to enhance G+C amplification (see, for example, Chakrabarti and Schutt (2002)). Such agents include, without limitation, tetramethylene sulfoxide (TMS); sulfolane; propyl sulfoxide; etc., for example at a concentration of from about 1% to about 7%, usually from about 3% to about 6%, and may be about 4% 4o about 5%, around about 4.5%. Such agents enhance the amplification of fragments with higher G+C ratios. Duplicate reactions may be performed in the absence and presence of a G+C enhancing agent.

The techniques of the present invention also provide a number of additional genetic manipulation technologies. The amplified product may be used for construction of complex cDNA libraries from extremely limited amounts of tissue, such as individual brain nuclei, tissue sections, and even single cells. The product can also be used as a source of large amounts of material for use as driver in subtractive hybridization.

The expression signature obtained by the methods of the invention find particular use in the study of gene expression in essentially any mammalian cell or cell population. Although the cell may be from blood (e.g., white cells, such as T or B cells), other sources include solid organs, such as brain, spleen, bone, heart, vascular, lung, kidney, liver, pituitary, endocrine glands, lymph node, dispersed primary cells, tumor cells, or the like. For example, the expression signature of tumor cells may be compared to their normal counterparts.

For example, a labeled product of the present methods may be hybridized to a microarray for determination of patterns of gene expression in cells of interest. Each of the labeled samples is hybridized to an array of oligonucleotide probes. Hybridization is accomplished according to methods well known in the art. Hybridization can be carried out under conditions varying in stringency, preferably under conditions of high stringency, e.g. 6X SSPE, 65° C., to allow for hybridization of complementary sequences having extensive homology.

High density microarrays of oligonucleotides are known in the art and are commercially available. The sequence of oligonucleotides on the array will correspond to the target sequences of interest. Arrays may comprise at least about $10^3$ different sequences, usually at least about $10^4$ different sequences, and may comprise $10^5$ or more different sequences. The length of oligonucleotide present on the array is an important factor in how sensitive hybridization will be to the presence of a mismatch, and may vary from about 12 to about 100 nt in length.

In a one embodiment, the microarrays are gene expression probe arrays. Such arrays comprise oligonucleotide probes derived from the sequence of annotated open reading frames in the genome of interest, from about 10% of the open reading frames, to as high as 75% or 95% of the annotated open reading frames. Commercially available high-density arrays containing a large number of oligonucleotide probes from genomic DNA sequence have been designed and used to monitor gene expression, e.g. in yeast, humans, etc.

Microarrays can be scanned to detect hybridization of the labeled samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734 (herein incorporated by reference). A scanning laser microscope is described in U.S. Pat. No. 5,445,934, supra. A scan, using the appropriate excitation line, is performed for each fluorophore used. The digital images generated from the scan are then combined for subsequent analysis. For any particular array element, the ratio of the fluorescent signal from one Nucleic acid sample is compared to the fluorescent signal from the other Nucleic acid sample, and the relative signal intensity determined.

Among the other uses of the present methods is the generation of material for SNP analysis. An emerging class of markers for genetic analysis are the single nucleotide polymorphism and other simple polymorphisms, e.g. deletions, double nucleotide polymorphisms, etc. SNPs are generally biallelic systems, that is, there are two alleles that a population may have for any particular marker. This means that the information content per SNP marker is relatively low when compared to microsatellite markers, which may have upwards of 10 alleles. SNPs also tend to be very population-specific; a marker that is polymorphic in one population may not be very polymorphic in another.

SNP markers offer a number of benefits that will make them an increasingly valuable tool. SNPs, found approximately every kilobase (see Wang et al. (1998) *Science* 280:1077-1082), offer the potential for generating very high density genetic maps, which will be extremely useful for developing haplotyping systems for genes or regions of interest, and because of the nature of SNPs, they may in fact be the polymorphisms associated with the disease phenotypes under study. The low mutation rate of SNPs also makes them excellent markers for studying complex genetic traits.

The materials for use in the methods of the present invention are ideally suited for preparation of kits produced in accordance with well known procedures. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primers of the present invention. The cognate restriction enzymes may also be provided. A set of instructions will also typically be included.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the array" includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Materials and Methods

RNA isolation. Frozen tissue samples (150 mg) were ground to a fine powder under liquid nitrogen in a mortar and pestle. The powder was processed using an RNEasy Midi Kit (Qiagen, Valencia, Calif.). Samples were treated with DNAse during the column purification procedure. Total RNA samples were analyzed using Agilent's (Palo Alto, Calif.) 2100 Bioanalyzer system for 18S and 28S band integrity. Messenger RNA was isolated using Boehringer-Mannheim's (Gaithersburg, Md.) magnetic bead isolation kit essentially according to manufacturer's instructions. The bound mRNA was washed extensively with high salt buffer and eluted with water. The purity and quantity of mRNA were estimated by $A_{260}/A_{280}$ nm readings.

RFA Amplicon synthesis: Double stranded cDNA is synthesized from 5 μg of total RNA was used as template in the Roche (Indianapolis, Ind.) cDNA Synthesis System according to manufacturer's instructions.

Probe synthesis: Disease and normal driver (amplicon) populations were biotin-labeled to high specificity using Invitrogen's BioPrime labeling kit. Manufacturer's instructions were followed with the following exceptions: one microgram of template was used, and the label reactions were incubated for 90 to 120 minutes. The biotinylated product was purified away from free dNTPs and primer with BD Bioscience/Clontech's (Palo Alto, Calif.) Chromaspin TE-100 size exclusion columns. The average yield for probe synthesis was 10-12 μg/reaction as determined by biotin quantitation using KPL's (Gaithersburg, Md.),probe biotinylation kit.

Amplicon probe synthesis: Ten percent of each cDNA reaction (normal and diseased from all patients) was digested with DpnII and ligated to an excess of R-Bgl-12/24 linker. The resulting linkered cDNA was amplified essentially as described in the RDA amplicon generation protocol, with the following modifications. All amplifications contained 5 units of Taq polymerase/100 μl reaction. cDNA concentrations were calculated based on the input of total RNA assuming 2% poly-A mRNA and 100% cDNA synthesis efficiency. Test amplifications were performed to determine cycle count threshold for optimum amplicon generation to achieve between 2 and 6 μg of amplicon per 100 μl reaction, and 18 cycles of amplification were established as the optimum for 1 μl of 6 μg/ml target. Disease and normal amplicons were pooled, ethanol precipitated and quantitated by $A_{260}$ and checked for purity by $A_{260}/A_{280}$ ratio.

Purified amplicons were biotin-labeled to high specificity using Invitrogen's BioPrime labeling kit. Manufacturer's instructions were followed with the following exceptions: one microgram of template was used, and the label reactions were incubated for 90 to 120 minutes. The biotinylated product was purified away from free dNTPs and primers with BDBioscience/Clontech's (Palo Alto, Calif.) Chromaspin TE-30 size exclusion columns pre-equilibrated with 2XSSC/0.1% SDS. The average yield for probe synthesis was 10-12 μg/rxn per μg template as determined by biotin quantitation using KPL's (Gaithersburg, Md.) probe biotinylation kit.

cDNA and amplicon synthesis methods: cDNA was synthesized from 5 to 10 μg of total RNA isolated from normal and disease tissue using a Roche cDNA synthesis kit with a novel poly-T primer that included DpnII and NlaIII restriction sites. The cDNA was cleaned and precipitated according to manufacturer's instructions, and resuspended in 30 to 50 μl of TE×10$^{-1}$. In the case of patient VNM277, concentration of normal and disease cDNAs was estimated by ethidium bromide quantitation with known standards.

A small amount of each cDNA (approximately 25 ng in the case of VNM277, ⅙th of the resuspended cDNA in the case of VNM285) was digested in separate reactions with DpnII or NlaIII. Digests were heat-killed, and appropriate linkers were added to each reaction (sequences available upon request). Approximately 1/100 of the VNM277 digest-ligation reactions, and 1/10 of the VNM285 digest-ligation reactions were used as template in amplicon synthesis. 8 to 12 tubes of 100 μl each were amplified essentially as described by with the following modifications. All amplifications contained 5 units of Taq polymerase/100 μl reaction and 100 pM R-Bgl-24 primer. VNM285 template was amplified for 28 cycles, and VNM277 template was amplified for 25 cycles. Reactions were pooled, phenol/chloroform extracted, ethanol-precipitated, and resuspended in 100 μl of TE×10$^{-1}$. Amplicon concentration was measured by $A_{260}$ absorbance, and purity was checked by $A_{260}/A_{280}$.

TagMan methods: Amplicons were diluted to 2 (VNM285) or 5 (VNM277) ng/μl in tRNA buffer (10 mM Tris pH 8.0, 5 μg/ml purified yeast tRNA). Amplicons were then further diluted another 100-fold in tRNA buffer for use as template. cDNA was diluted 1/30 (VNM285) or 1/50 (VNM277) for use as template. Individual amplifications were performed in triplicate 30 μl reactions containing 90 nM external primers (sequences available upon request), 25 nM reporter probe, and 1.5 μl of template. Gene-specific quantitative calibration standards consisted of purified plasmids containing a DpnII restriction fragment of the gene amplified by the TaqMan primers. Plasmids were purified and diluted in tRNA buffer to establish a dilution series of 2×10$^7$ copies/μl, 2×10$^6$ copies/μl, and 2×10$^5$ copies/μl for each gene fragment assay. Each test gene was assayed in parallel with actin. Reactions were run on an ABI 7700 thermocycler. Each gene fragment was analyzed at least twice.

Copy numbers for each patient sample (normal and disease, amplicons and cDNA) were averaged and analyzed in Microsoft Excel. Values that exceeded four times the standard deviation for any sample were removed. The remaining data always consisted of at least four values per sample. New averages and standard deviations were calculated for each sample, and each sample dataset was confirmed to have a coefficient of variation below 40%. Amplicon copies for the test genes were adjusted based upon measured actin levels in cDNA compared to amplicon. Corrected disease/normal ratios derived from cDNA and amplicon templates for each gene fragment were averaged, and coefficients of variation between the ratios for the cDNA and amplicon templates were calculated for each gene fragment.

Fold amplification calculations: Fold amplification values as determined by copy number were calculated by multiplying average copy numbers from known dilutions of template by appropriate dilution factors to determine the equivalent number of copies present in, or generated from, 1 μl cDNA. The resulting amplicon copy numbers were then divided by the resulting cDNA copy numbers. Average amplicon copy numbers were multiplied essentially as shown in Panel 6, using numbers appropriate to the sample. Average cDNA copy numbers were divided by 1.5, then multiplied by 30 (patient VNM285) or 50 (patient VNM277) to determine the number of copies present in 1 μl undiluted cDNA.

Disease/normal ratio calculations: Average amplicon copies for each test gene were adjusted based upon measured actin levels in the cDNA as compared to actin levels in the amplicon, for each patient. Disease/normal ratios were calculated for each test gene in each patient using the corrected copy numbers.

Biotinylation of amplicon: 0.5 μg each of DpnII and NlaIII amplicons from normal or disease samples were pooled and used as template in each of 4 parallel biotinylations with Invitrogen's BioPrime biotinylation kit. Reactions were carried out for 4 hours and pooled. Reactions were concentrated to a volume of 50 μl using Microcon YM-30 spin columns. Concentration was measured by $A_{260}$ absorbance, and purity was checked by $A_{260}/A_{280}$.

Microarray hybridization and analysis: 10 μg of biotinylated amplicon was hybridized to U133A+B chips according to standard protocols by Stanford Protein and Nucleic Acid Facility staff. Resulting intensity values were imported into Excel. Values from the disease sample of a chip were divided by the values from the normal sample of the same patient of the same patient to determine degree of up- or down-regulation.

Results

Amplification of small fragments generated by cutting cDNA with Dpn II (a four base cutter) and the addition of synthetic linkers (primers) to the ends of these fragments has been established as a robust method to generate to generate driver and tester amplicon in the Representational Differential Analysis (RDA) protocol (Huband and Schatz (1994) N.A.R. 22:5640-5648).

In the process of validating this amplicon for the use as a probe to confirm expression results from RDA subtraction, the amplification process was determined to be extremely linear and provide for efficient amplification.

Conventional methods of RDA analysis are to: 1) synthesize double stranded DNA, 2) digest with DpnII to generate small fragments, 3) add Non-phosphorylated linkers to cDNA fragments, and 4) amplify Tinkered fragments by 20 cycles of PCR. However, such methods lose information at the 5' and 3' end, which is cleaved by DpnII.

Figure 1:
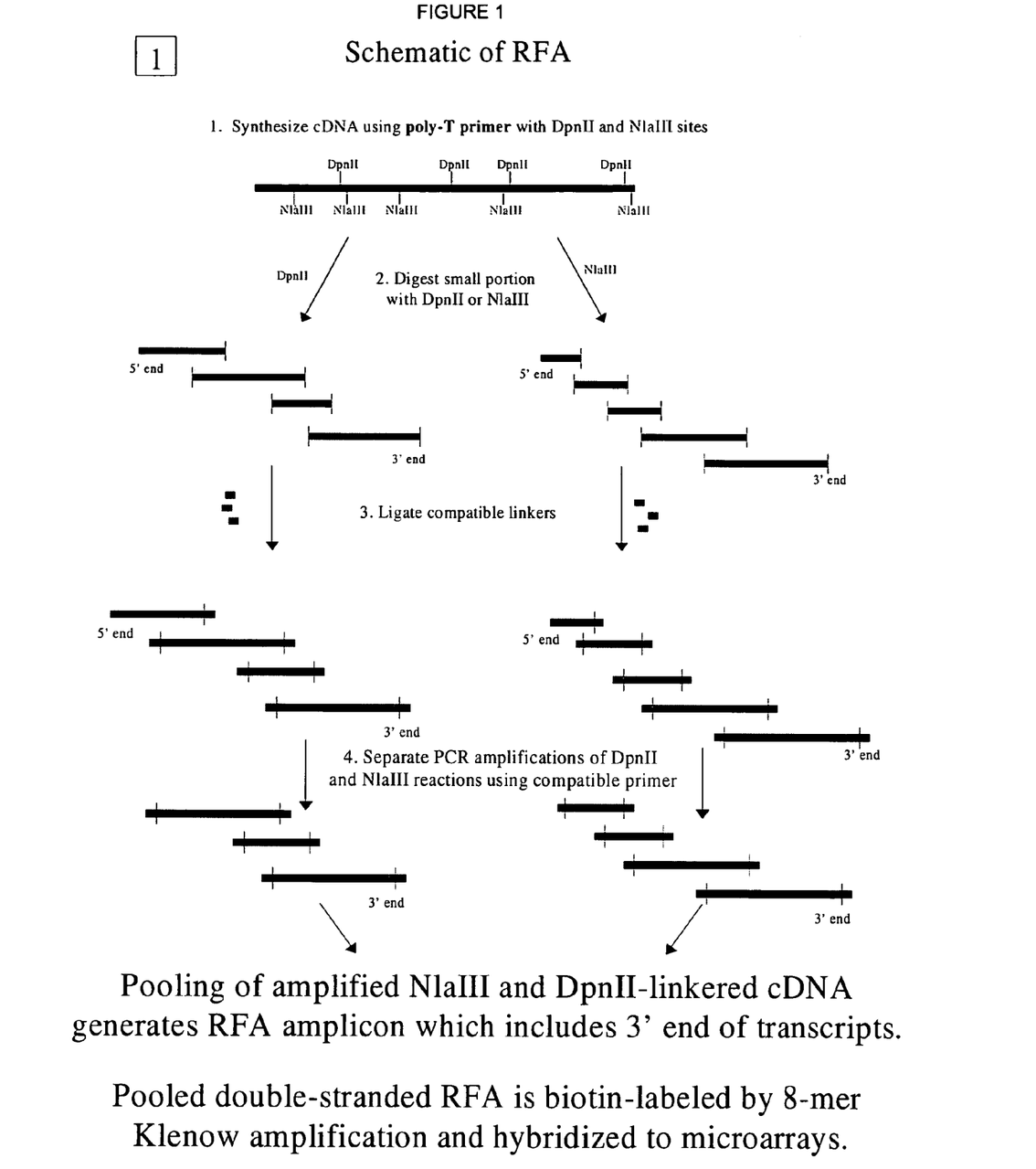
FIG. 1 is a schematic depicting an example of RFA.
Figure 2:
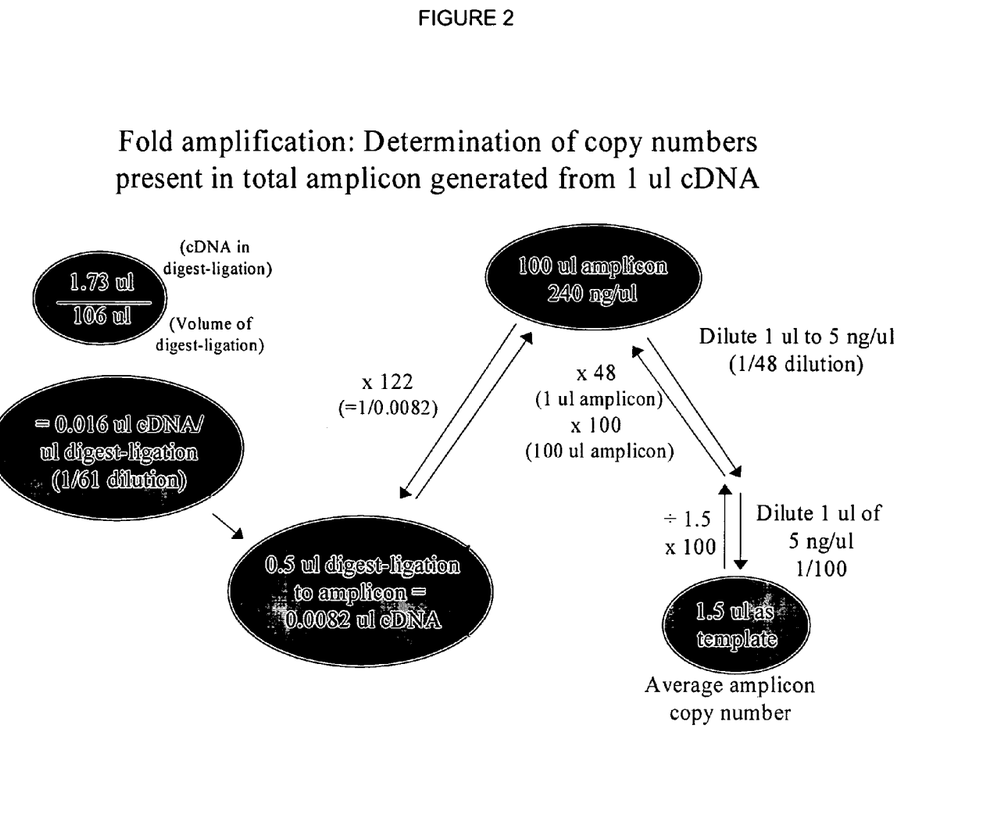
Figure 3:
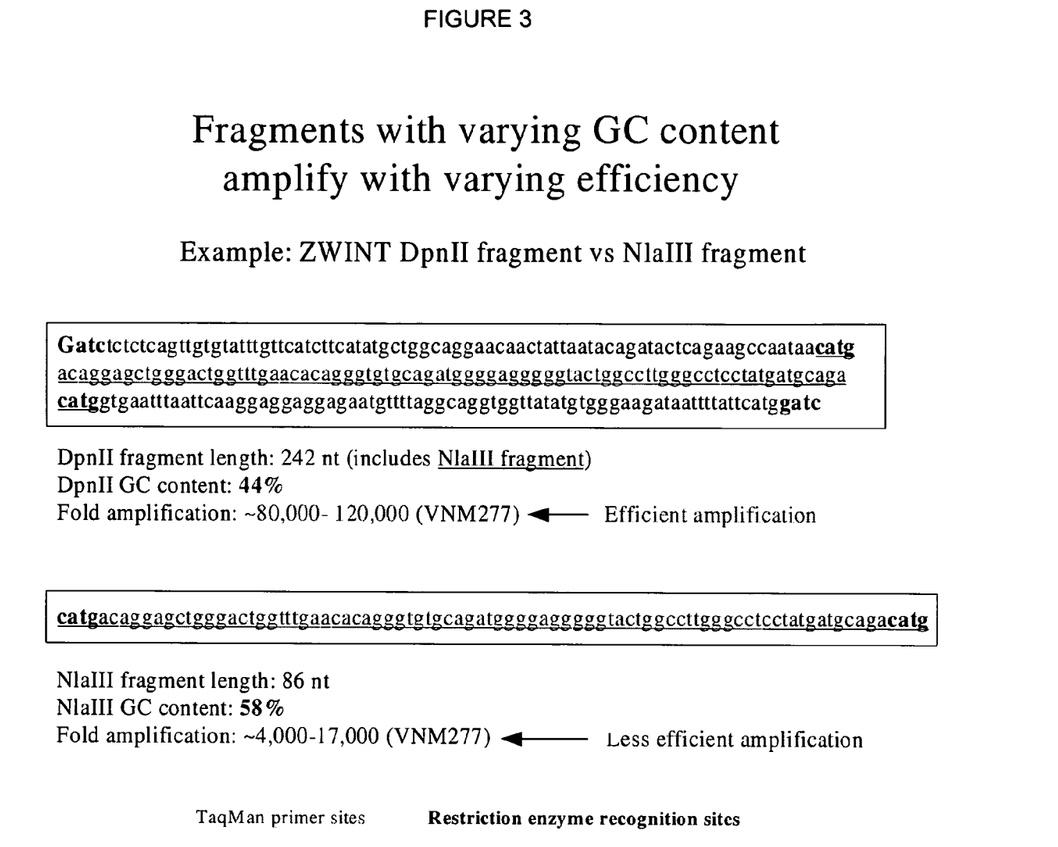
FIG. 3 shows the effect of GC content on amplification.
Figure 4:
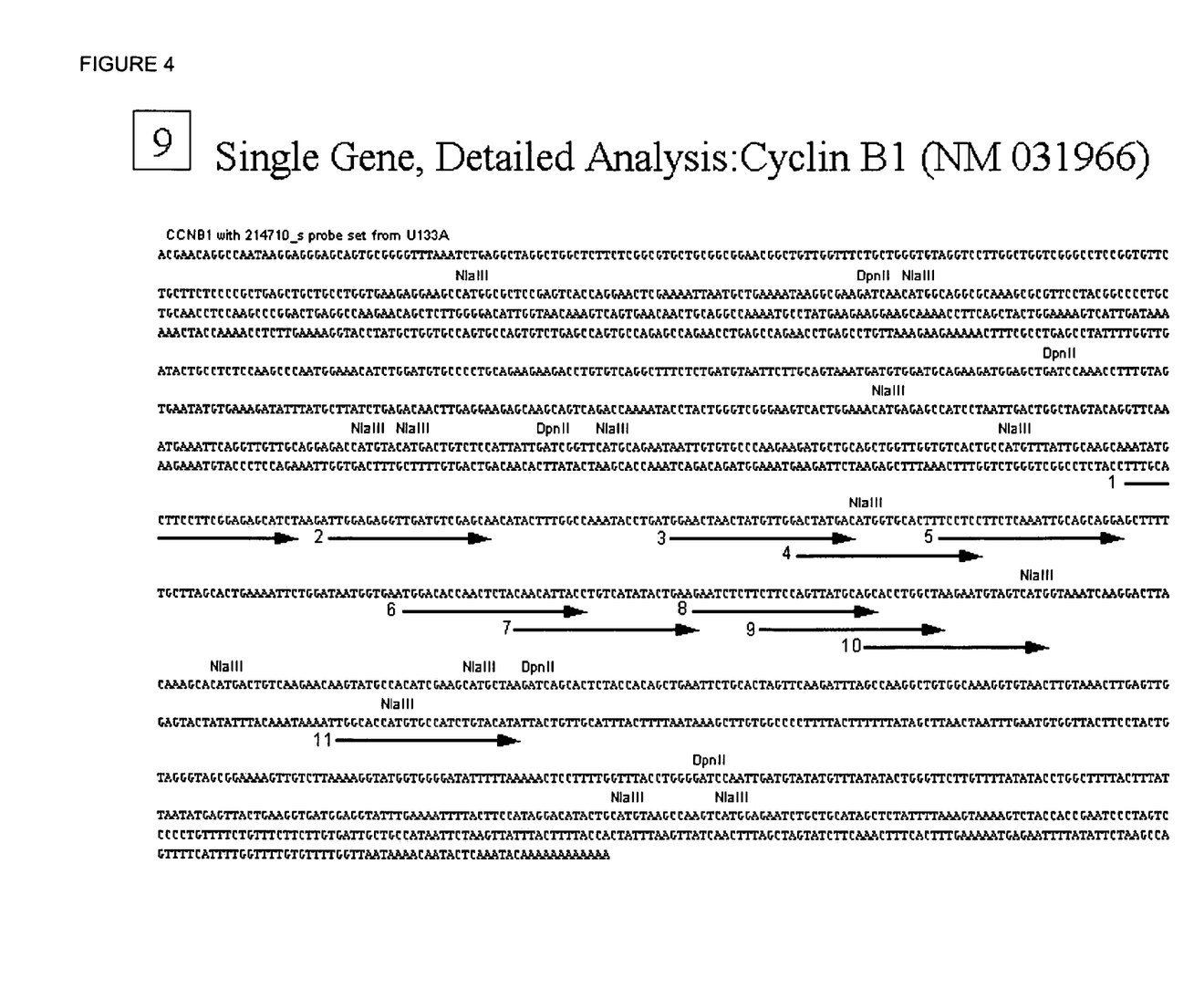
FIG. 4 shows analysis of cyclin B1
Figure 5:
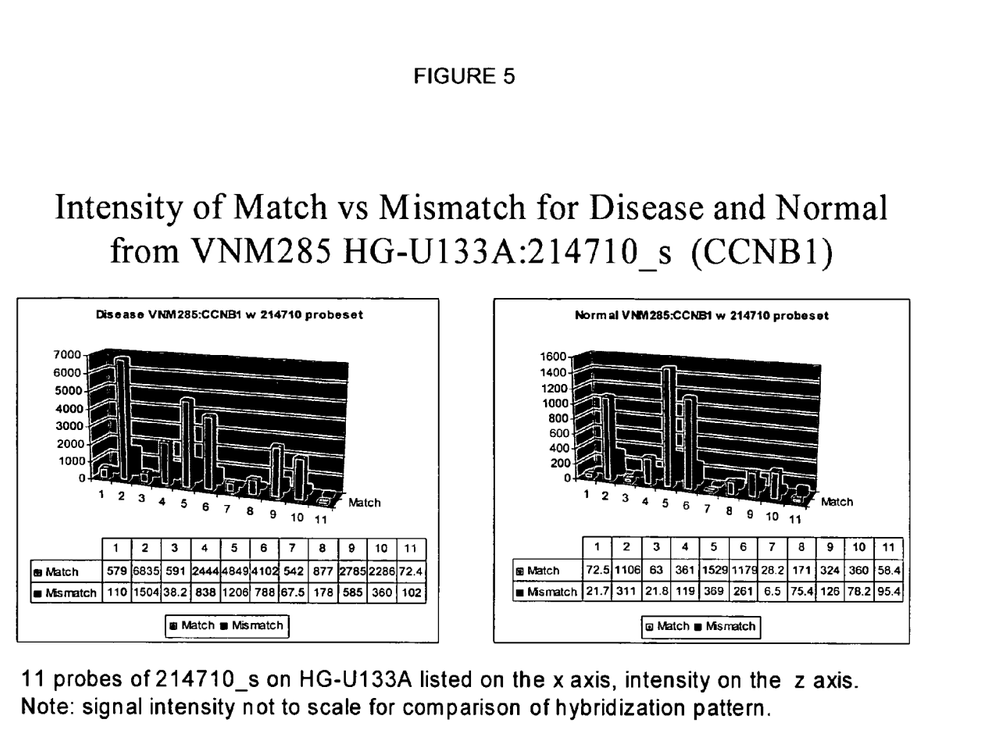
FIG. 5 shows the intensity of match v. mismatch for diseased and normal cells.
Figure 6:
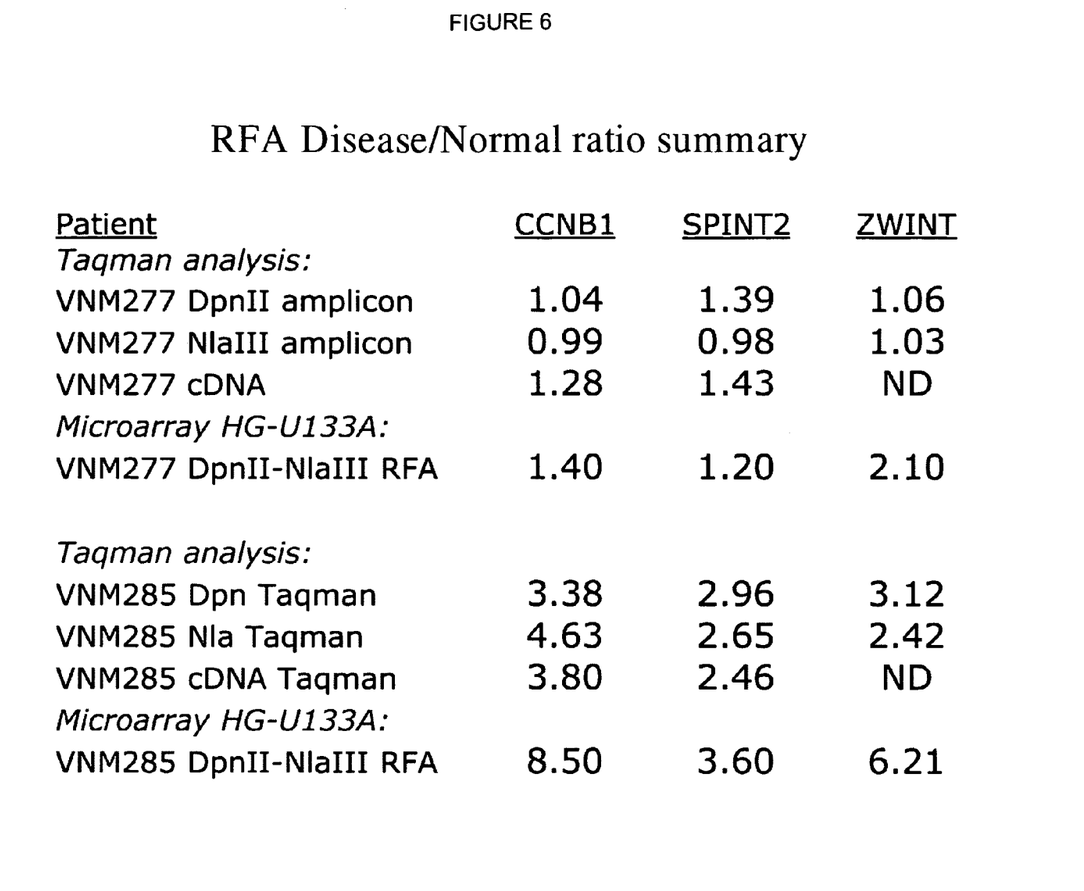
FIG. 6 shows the corrected intensity to scale of disease and normal match.
Figure 7:
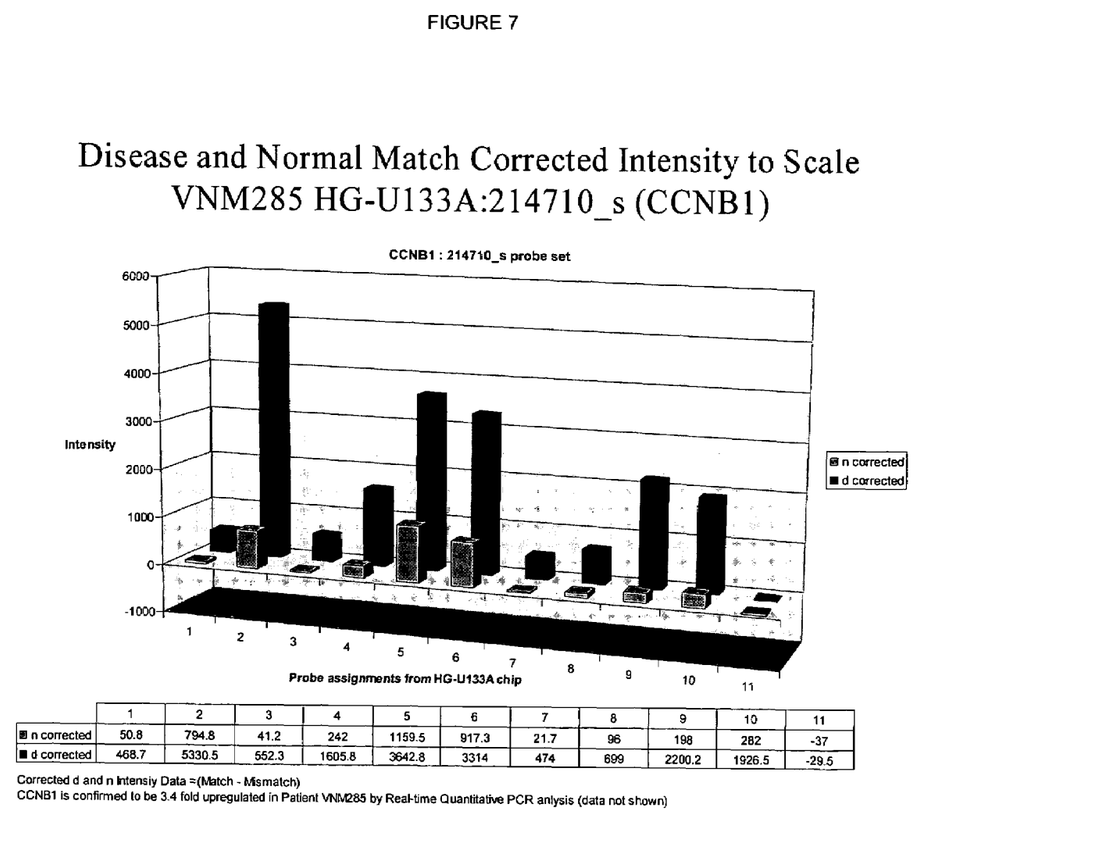
FIG. 7 is a summary of RFA disease/normal ratios.

The protocol has been improved by steps that allow retention of the 5' and 3' ends, thereby providing for a complete representation of the amplified sequence. The protocol for representational fragment amplification (RFA) has comprised the steps of 1) synthesizing double stranded DNA with a modified oligo dT primer containing NlaIII/DpnII restriction sites, 2) adding DpnII or NlaIII linkers to the 5' ends of the double stranded cDNA, 3) digesting with DpnII or NlaIII to generate small fragments, 4) adding Non-phosphorylated linkers to the small cDNA fragments, 5) amplifying linkered fragments with a single primer for 20-30 cycles of PCR. The hybrid primer comprising both NlaIII/DpnII restriction sites is (SEQ ID NO:1) PolyT18_dpn/nla-V; GAGAGTGAGTGATCATGTTTTTTTTTTTTTTTTTV A schematic of the process is shown in FIG. 1. The improvements to the invention allow the amplification of the complete expression signature with no loss of information from the 5' and 3' ends. This improvement allows the generation of the most informative and accurate representation of the pool of sequences being tested, e.g. the expression signature of a cell, tissue, organism, etc. Alternate methods of attaching DpnII and NlaIII to the 3' end of cDNA during synthesis may also be used.

and actin for normal and disease samples using normal and disease amplicon and cDNA as template. Gene-specific and actin ladders were included. Calculated copy numbers based on the specific quantitative ladders were exported into an Excel spreadsheet for statistical analysis. Copy numbers for each patient sample (normal and disease) for both the test gene and actin were averaged and analyzed. Coefficients of variation for copy number/normal ratios were calculated for the test gene and for actin for cDNA and amplicon samples. Actin ratios were corrected to 1 for each sample, and the test gene ratios for each sample were multiplied by the appropriate actin correction factor to calculate corrected over-

```
PolyT18_dpn/nla-V    GAGAGTGAGTGATCATGTTTTTTTTTTTTTTTTTV                             (SEQ ID NO:2)

RFA T7 POLYT_NLAIII  AAACGACGGCCAGTGAATTGTAATACGACTCACTATAGGCcatgTTTTTTTTTTTTTTTTTV  (SEQ ID NO:3)

RFA T7 POLYT_ALUI    AAACGACGGCCAGTGAATTGTAATACGACTCACTATAGGCagctTTTTTTTTTTTTTTTTTV  (SEQ ID NO:4)

R-BGL-24             AGCACTCTCCAGCCTCTCACCGCA                                        (SEQ ID NO:5)

R-BGL-12             GATCTGCGGTGA                                                    (SEQ ID NO:6)

R-BGL-28_NlaIII      AGCACTCTCCAGCCTCTCACCGCACATG                                    (SEQ ID NO:7)

R-BGL-08_AluI        TGCGGTGA                                                        (SEQ ID NO:8)

alu_linker-f         CCGGGCACGAGCT                                                   (SEQ ID NO:9)

Nla-linker-f         CCGGGCACGCATG                                                   (SEQ ID NO:10)

alu_linker-r         P-AGCTCGTGCCCG                                                  (SEQ ID NO:11)

Nla-linker-r         P-CATGCGTGCCCG                                                  (SEQ ID NO:12)

RFA LINKER-f         P-GATCGCCC                                                      (SEQ ID NO:13)

RFA LINKER-r         GGGGGCGATC                                                      (SEQ ID NO:14)

R-Dpn-24/12

R-BGL-24             AGCACTCTCCAGCCTCTCACCGCA                                        (SEQ ID NO:15)

R-BGL-12             GATCTGCGGTGA                                                    (SEQ ID NO:16)

R-Nla 28/08

R-BGL-28_NlaIII      AGCACTCTCCAGCCTCTCACCGCACATG                                    (SEQ ID NO:17)

R-BGL-08_AluI        TGCGGTGA                                                        (SEQ ID NO:18)
```

Comparison of disease/normal expression ratios in cDNA and RFA amplicon. Double-stranded cDNA was synthesized from normal and disease samples from patient VNM285 using 6 µg total RNA and a poly-T-based primer (5'-GAGAGTGAGTGATCATGTTTTTTTTTTTTTTTTTV-3'; SEQ IID NO:2) in the Roche synthesis system, and amplicon was generated as described above from 1/10 of the synthesized cDNA, divided in half to accommodate both DpnII and NlaIII amplicon generation. Real-time quantitative RT-PCR was performed using normal and disease amplicons and cDNA as template for CCNB1, SPINT2, and ZWINT using the primers and probes as described above. Amplicons were diluted to 0.2 ng/µl in tRNA buffer, and cDNA was diluted to 1/30 in tRNA buffer. Gene-specific dilution ladders consisted of plasmid containing the gene fragment being amplified, diluted to $2 \times 10^7$ copies/µl, $2 \times 10^6$ copies/µl, and $2 \times 10^5$ copies/µl in tRNA buffer. 30 µl reactions as noted above were performed in triplicate. Assays were performed such that each plate tested a selected gene expression ratios. Corrected over-expression ratios derived from cDNA and amplicon templates were compared as shown in Table 1.

TABLE 1

| Clone # | Gene name | Disease/normal ratio | | | StdDev | Coeff of Var |
|---|---|---|---|---|---|---|
| | | NlaIII amplicon | DpnII amplicon | cDNA | | |
| 187 | CCNB1 | 4.5 | 4.36 | 5.44 | 0.59 | 12.3% |
| 50 | SPINT2 | 2.6 | 2.57 | 3.28 | 0.40 | 14.3% |
| 29 | ZWINT | 2.71 | 3.34 | 3.42 | 0.39 | 12.3% |

Quantitative RT-PCR analysis is used to determine relative ratio of gene expression for Disease / Normal ratios derived from triplicate sample of real time quantitative PCR. The ratio values for the three genes are reported and show good correlation to starting cDNA ratio also reported here. Dilution of linker ligated cDNA was amplified 25 cycles to generate greater than 40 µg of RFA amplicon from less than 2 ng of cDNA.

RFA Amplification of Cyclin B 1 (CCNB1)

|  | Average copies | Multiplier to 1 ul cDNA | Effective copies from 1 ul cDNA | Approximate fold amplification | Sample | Actin-corrected disease/normal |
|---|---|---|---|---|---|---|
| Patient VNM277 | | | | | | |
| DpnII N | 77,951 | 3.33E + 07 | 2.60E + 12 | 407,340 | VNM277 cDNA | 1.04 |
| NlaIII N | 23,079 | 5.86E + 07 | 1.35E + 12 | 212,348 | VNM277 DpnII amplicon | 0.99 |
| cDNA N | 127,459 | 50 | 6.37E + 06 |  | VNM277 NlaIII amplicon | 1.28 |
| DpnII D | 93,445 | 5.85E + 07 | 5.46E + 12 | 330,886 | VNM277 average ratio | 1.10 |
| NlaIII D | 61,185 | 4.08E + 07 | 2.50E + 12 | 151,319 | Coefficient of variation | 13.94% |
| cDNA D | 330,320 | 50 | 1.65E + 07 |  |  |  |
| Patient VNM285 | | | | | | |
| DpnII N | 28,434 | 3.12E + 06 | 8.87E + 10 | 94,803 | VNM285 cDNA | 3.38 |
| NlaIII N | 15,421 | 2.78E + 06 | 4.29E + 10 | 45,812 | VNM285 DpnII amplicon | 4.63 |
| cDNA N | 31,192 | 30 | 9.36E + 05 |  | VNM285 NlaIII amplicon | 3.80 |
| DpnII D | 126,996 | 2.81E + 06 | 3.57E + 11 | 71,418 | VNM285 average ratio | 3.94 |
| NlaIII D | 66,625 | 2.98E + 06 | 1.99E + 11 | 39,734 | Coefficient of variation | 16.13% |
| cDNA D | 166,558 | 30 | 5.00E + 06 |  |  |  |

RFA Amplification of Serine-protease Inhibitor, Kunitz Type 2 (SPINT2)

|  | Average copies | Multiplier to 1 ul cDNA | Effective copies from 1 ul cDNA | Approximate fold amplification | Sample | Actin-corrected disease/normal |
|---|---|---|---|---|---|---|
| Patient VNM277 | | | | | | |
| DpnII N | 7,176 | 3.33E + 07 | 2.39E + 11 | 57,764 | VNM277 cDNA | 1.39 |
| NlaIII N | 51,120 | 5.86E + 07 | 3.00E + 12 | 724,568 | VNM277 DpnII amplicon | 0.98 |
| cDNA N | 82,741 | 50 | 4.14E + 06 |  | VNM277 NlaIII amplicon | 1.43 |
| DpnII D | 8,394 | 5.85E + 07 | 4.91E + 11 | 34,158 | VNM277 average ratio | 1.27 |
| NlaIII D | 158,781 | 4.08E + 07 | 6.49E + 12 | 451,300 | Coefficient of variation | 19.65% |
| cDNA D | 287,419 | 50 | 1.44E + 07 |  |  |  |
| Patient VNM285 | | | | | | |
| DpnII N | 2,922 | 3.12E + 06 | 9.12E + 09 | 8,994 | VNM285 cDNA | 2.96 |
| NlaIII N | 22,290 | 2.78E + 06 | 6.20E + 10 | 61,126 | VNM285 DpnII amplicon | 2.65 |
| cDNA N | 33,792 | 30 | 1.01E + 06 |  | VNM285 NlaIII amplicon | 2.46 |
| DpnII D | 7,629 | 2.81E + 06 | 2.14E + 10 | 4,549 | VNM285 average ratio | 2.69 |
| NlaIII D | 62,694 | 2.98E + 06 | 1.87E + 11 | 39,642 | Coefficient of variation | 9.47% |
| cDNA D | 157,098 | 30 | 4.71E + 06 |  |  |  |

RFA Amplification of ZW10 Interacting Factor (ZWINT)

|  | Average copies | Multiplier to 1 ul cDNA | Effective copies from 1 ul cDNA | Approximate fold amplification | Sample | Actin-corrected disease/normal |
|---|---|---|---|---|---|---|
| Patient VNM277 | | | | | | |
| DpnII N | 908 | 3.33E + 07 | 3.02E + 10 | 119,637 | VNM277 cDNA | 1.06 |
| NlaIII N | 75 (noise) | 5.86E + 07 | 4.40E + 09 | 17,392 | VNM277 DpnII amplicon | 1.03 |
| cDNA N | 5,057 | 50 | 2.53E + 05 |  | VNM277 NlaIII amplicon | ND |

-continued

| | Average copies | Multiplier to 1 ul cDNA | Effective copies from 1 ul cDNA | Approximate fold amplification | Sample | Actin-corrected disease/normal |
|---|---|---|---|---|---|---|
| DpnII D | 1,079 | 5.85E + 07 | 6.31E + 10 | 83,068 | VNM277 average ratio | 1.04 |
| NlaIII D | 80 (noise) | 4.08E + 07 | 3.27E + 09 | 4,298 | Coefficient of variation | 2.23% |
| cDNA D | 15,200 | 50 | 7.60E + 05 | | | |

Patient VNM285

| | | | | | | |
|---|---|---|---|---|---|---|
| DpnII N | 140 | 3.12E + 06 | 4.36E + 08 | 19,011 | VNM285 cDNA | 3.12 |
| NlaIII N | 32 (noise) | 2.78E + 06 | 8.98E + 07 | 3,913 | VNM285 DpnII amplicon | 2.42 |
| cDNA N | 765 | 30 | 2.29E + 04 | | VNM285 NlaIII amplicon | ND |
| DpnII D | 327 | 2.81E + 06 | 9.19E + 08 | 8,140 | VNM285 average ratio | 2.77 |
| NlaIII D | 65 (noise) | 2.98E + 06 | 1.93E + 08 | 1,713 | Coefficient of variation | 17.64% |
| cDNA D | 3,764 | 30 | 1.13E + 05 | | | | noise, ND = none detected

The RFA samples were biotinylated as described above and hybridized to Affymetrix U133a and U133b chip sets in order to validate the use of the samples with microarrays. The results of analysis for the genes that we have previously quantitated by RT-PCR were in good agreement. Two chip sets were run and compared in order to determine the need for dual enzyme applications. The NlaIII oligos were designed to generate a more complete and assayable RFA, and the benefit of the two enzyme design was predicted by the restriction digest analysis of several genes. The DpnII RFA and the NlaIII RFA are combined 50/50 and compared to the DpnII RFA alone. It is predicted that certain genes will have numerous DpnII sites within the gene and or the probe set, and that the combination of the DpnII RFA with the NlaIII RFA can compensate for the high restriction site by providing an alternative representative fragments.

Analysis of the U133 A and B chips that were hybridized with probe containing amplicon from Dpn digests and amplicon prepared from an equal mixture of Dpn and Nla digests showed marked improvement in RMA based intensity values for a large number of genes. The calculation represented below are from A chip set comparing disease_Dpn and disease_Dpn/Nla hybridizations.

Results: There are 22,283 probes on the A chip, and 638 probe set demonstrated greater than two fold increase in signal. The fold signal increase ranged from 2.001 to 13.56 and demonstrates that the two enzyme system can improve the detection for a significant percentage of the probe sets. Only 60 probe set showed greater than 2 fold decrease in signal, which is limited because 50% of the probe is contained in the comparison sample.

TABLE 2

| Gene ID | Dpn | Dpn/Nla | % difference | Fold difference |
|---|---|---|---|---|
| 212077_at | 103 | 519 | 1.34 | 5.04 |
| 201673_s_at | 195 | 994 | 1.34 | 5.09 |
| 200883_at | 113 | 575 | 1.34 | 5.10 |
| 201345_s_at | 184 | 938 | 1.35 | 5.11 |
| 221664_s_at | 297 | 1538 | 1.35 | 5.17 |
| 200897_s_at | 125 | 649 | 1.35 | 5.18 |
| 200706_s_at | 234 | 1213 | 1.35 | 5.19 |
| 215450_at | 164 | 857 | 1.36 | 5.23 |
| 200892_s_at | 270 | 1434 | 1.37 | 5.31 |
| 203243_s_at | 18 | 95 | 1.37 | 5.31 |
| 202779_s_at | 473 | 2525 | 1.37 | 5.34 |
| 202043_s_at | 234 | 1264 | 1.37 | 5.40 |
| 203316_s_at | 259 | 1418 | 1.38 | 5.47 |
| 201641_at | 857 | 4738 | 1.39 | 5.53 |
| 200809_x_at | 2009 | 11128 | 1.39 | 5.54 |
| 201923_at | 147 | 833 | 1.40 | 5.67 |
| 201267_s_at | 315 | 1806 | 1.41 | 5.72 |
| 201021_s_at | 363 | 2080 | 1.41 | 5.73 |
| 217719_at | 372 | 2140 | 1.41 | 5.75 |
| 217927_at | 185 | 1063 | 1.41 | 5.75 |
| 221532_s_at | 284 | 1650 | 1.41 | 5.81 |
| 206032_at | 197 | 1175 | 1.43 | 5.96 |
| 217971_at | 36 | 212 | 1.43 | 5.98 |
| 218277_s_at | 116 | 715 | 1.44 | 6.16 |
| 221622_s_at | 131 | 839 | 1.46 | 6.40 |
| 201410_at | 32 | 205 | 1.47 | 6.50 |
| 209861_s_at | 249 | 1649 | 1.48 | 6.62 |
| 215952_s_at | 694 | 4747 | 1.49 | 6.83 |
| 200933_x_at | 1459 | 10430 | 1.51 | 7.15 |
| 219759_at | 150 | 1238 | 1.57 | 8.26 |
| 200730_s_at | 36 | 329 | 1.60 | 9.06 |
| 214395_x_at | 706 | 7385 | 1.65 | 10.46 |
| 208810_at | 119 | 1259 | 1.65 | 10.56 |
| 209009_at | 77 | 882 | 1.68 | 11.38 |
| 207791_s_at | 84 | 1135 | 1.73 | 13.56 |

TABLE 3

| Gene | Probeset | Chip | Sample | Normal Intensity | P/A/M | Disease intensity | P/A/M | Chip Dis/Normal | TaqMan Dis/Normal |
|---|---|---|---|---|---|---|---|---|---|
| G1P2 | 205483_s_at | A | Dpn/Nla | 6836 | P | 8304 | P | 1.2 | 1.8 |
| AURKB | 209464_at | A | Dpn/Nla | 593 | P | 1379 | P | 2.3 | 5.5 |
| KRT16 | 209800_at | A | Dpn/Nla | 5546 | P | 6240 | P | 1.1 | 1.7 |
| CDCA8 | 221520_s_at | A | Dpn/Nla | 170 | M | 495 | P | 2.9 | 2.6 |
| KRT14 | 209351_at | A | Dpn/Nla | 11958 | P | 14380 | P | 1.2 | 2 |
| CCNB1 | 214710_s_at | A | Dpn/Nla | 430 | P | 1934 | P | 4.5 | 4.8 |
| ZWINT | 204026_s_at | A | Dpn/Nla | 107 | P | 321 | P | 3.0 | 3.3 |
| SPINT2 | 210715_s_at | A | Dpn/Nla | 1905 | P | 3539 | P | 1.9 | 3.8 |
| KARS | 200840_at | A | Dpn/Nla | 539 | P | 940 | P | 1.7 | 0.9 |
| OAZ1 | 215947_s_at | A | Dpn/Nla | 299 | P | 499 | P | 1.7 | 1.3 |
| OAZ1 | 215952_s_at | A | Dpn/Nla | 4175 | P | 4329 | P | 1.0 | 1.3 |

Example 2

The source of cDNA to be digested and linkered was always 500 µg/ml, as determined by the 25 ng cDNA in the 50 ml ligation volume, unless otherwise noted. Sample 19206 normal and disease tissues were processed for Total RNA by the Qiagen RNeasy midi kit, and 5 mg of total RNA was used to synthesize cDNA with the modified oligo-dT method previously described. Two aliquots of cDNA were digested with DpnII or NlaIII, the reactions were heat killed and cooled for linker ligation. Dpn III and Nla III specific linkers were ligated to the digested cDNA for 90 minutes in 50 ul volume of 1x Quick ligase (New England Biolabs).

Two methods of amplification were employed, which offered distinct advantages. Non-TMS amplification, as described above, is a Taq polymerase reaction that has all of the normal characteristics of Taq reactions. The TMS based reaction modifies Taq polymerase amplification method by the addition of 4.5% Tetramethylene Sulfoxide (TMS) added to enhance the amplification of fragments with higher G+C ratios (Chakrabarti and Schutt (2002) Biotechniques 32(4): 866, 868, 870-2, 874). Other agents that can enhance G+C amplification inhibition (Chakrabarti and Schutt (2001) Gene 274(1-2): 293-8) include, without limitation, sulfolane and propyl sulfoxide.

TABLE 4

| RFA buffer conditions | Tms 1x | 50x | 34x | Norm 1x | 50x | 34x |
|---|---|---|---|---|---|---|
| 10 x RDA buffer | 10 | 500 | 340 | 10 | 500 | 340 |
| 10 mM each dNTP (50x) | 2 | 100 | 68 | 2 | 100 | 68 |
| R-BGL-24 (100 uM) | 1 | 50 | 34 | 1 | 50 | 34 |
| TMS (Tetramethylene Sulfoxide) | 4.5 | 225 | 153 | 0 | 0 | 0 |
| H₂O | 72.5 | 3625 | 2465 | 77 | 3850 | 2618 |
| | 90 | 4500 | 3060 | 90 | 4500 | 3060 |

All reactions were performed with a hot start protocol, in which Taq polymerase is diluted to 0.5 Units/µl in water (room temp) and 10 µl is added to the reaction after 10 minutes of sample equilibration at 70 or 72 degrees C.

Typically a master mix for the entire plate was prepared, in this case 3400 µl of both TMS and non-TMS reagents were prepared and 760 µl was aliquoted into 1.5 ml eppendorf tubes for the addition of template. These reactions with 19206 each received 1 µl of cDNA target per 760 µl of master mix tube. 12×200 µl tubes each get 90 µl of master mix target for each of the 12 set reaction performed for RFA amplification.

TABLE 5

| Plate organization Non-TMS and TMS amplification | | | | |
|---|---|---|---|---|
| Dpn II normal | 12 tubes | 1100 ul | | |
| Dpn II disease | 12 tubes | 1100 ul | | |
| Nla III normal | 12 tubes | 1100 ul | | |
| Nla III disease | 12 tubes | 1100 ul | 4500 ul | Master mix |
| TMS Dpn II normal | 12 tubes | 1100 ul | | |
| TMS Dpn II disease | 12 tubes | 1100 ul | | |
| TMS Nla III normal | 12 tubes | 1100 ul | | |
| TMS Nla III disease | 12 tubes | 1100 ul | 4500 ul | Master mix |

TMS and nonTMS amplifications were perfomed in separate thermocyclers as required because of the different temperature requirements. TMS reactions were cycled 22 cycles with times for 95 degree of 20 seconds, 70 degrees for 5 minutes, with a final 10 minute 72 degree incubation. The nonTMS reactions were cycled as previously described for 24 cycles. Target estimations for these amplifications are 5 µl of the linker ligations which corresponds to 2.5 ng of target per 12 tube setup. Common reactions are pooled and isopropanol precipitated in duplicate 2 ml microcentrifuge tubes, with 0.3 M Na Acetate, equal volume of isopropanol and chilled at −20 degree Celsius for 40 minutes or −80 for 20 minutes. Amplification products were pooled, phenol extracted, and-ethanol precipitated for further purification. DNA pellets were washed with 70% ethanol, dried briefly and resuspended in 200 µl TE 10-1 for accurate UV quantitation at the desired 1:10 water dilution.

Results : The average yield of RFA amplicon for these sets of experiments was 69.6 ug of DNA per set of 12 reactions.

In order to determine if the strand displacement synthesis was equally applied to all species or fragments with the RFA amplicon, two sets of 4×1 µg reactions were established with the same 19206 normal TMS RFA amplicon. The resulting probes were quantified by OD determination after purification through Amicon 30 spin column. Equal quantities were hybridized to two Affymetrix HG U133 plus 2.0 microarrays. The resulting CEL files from the hybridization analysis were imported into the ArrayAssist (Stratgene, Inc.) and converted to Master RMA files (Irizarry, et al. (2003). Biostatistics 4(2): 249-64). The Heatmap analysis allows the simple exporting of the RMA values to Microsoft Exel for additional characterization. The percent difference values were calculated by dividing the difference between the values by the mean of the values for each gene. The percent difference was used to sort the RMA intensity values.

Results: Comparison of RMA intensity values shows that 53,166 of 54,675 genes had % difference values of 25% or lower. This corresponds to 97.24% of the genes having a high degree of concordance for the values calculated for RMA intensity. The RMA algorithm is also available with the Bioconductor R-programming package for microarray analysis.

The dual enzyme system has advantages in improving signals for genes fragments which would have experienced difficulties during single enzyme amplification. These improvements can be attributed to variations in the location of G+C rich regions within fragments and changes in overall fragment lengths.

Summary Values for TMS Improvements

TMS validation of improvements: MicroArray experiments with sample 19206 and TMS testing are compared with previous microarray results that were performed without the TMS additive, in order to gain insights into the differences that can appear when TMS is introduced into the amplification protocols. General amplification rates for TMS at 70 degrees and non-TMS at 72 degrees were comparable in yields. Comparison of RMA intensity values from HG U133 plus 2.0 chips, TMS and non-TMS, shows certain probe sets improving.

Results: There are 54,675 probes sets on the Affymetrix U133 plus 2.0, and 4451 probes sets had decreased RMA values on the TMS normal sample of greater than 2 fold when the compared to the nonTMS RMA value. There were also 2088 probes sets that had an increase in greater than two fold when the RMA values for the TMS normal sample were compared the RMA values of the nonTMS sample. The range of fold improvement ranged from 2 to 22.9. The range of fold decrease was from 19.9 to 2.

What is claimed is:

1. A method for non-preferential replication of a starting pool of nucleic acids, the method comprising:
   synthesizing cDNA from said starting pool, utilizing an oligo dT primer comprising restriction sites at least one frequent cutter restriction enzyme;
   synthesizing a DNA strand complementary to said cDNA to produce double stranded DNA;
   ligating linkers comprising restriction sites for said at least one frequent cutter restriction enzyme to the 5' end of said double stranded DNA;
   digesting the product of said ligating step with said frequent cutter restriction enzyme;
   ligating non-phosphorylated linkers to fragments of said digesting step;
   amplifying the product of said ligating step with a single primer;
   wherein the product of said amplifying step is non-preferentially amplified about $10^3$-fold from said starting pool and where the representation of species does not vary by more than 50% between the starting pool and the amplified product.

2. The method of claim 1, wherein said product of said amplifying step is non-preferentially amplified about $10^4$-fold from said starting pool.

3. The method of claim 1, wherein said oligo dT primer comprises restriction sites for two or more frequent cutter restriction enzymes; said linkers comprise restriction sites for said two or more frequent cutter restriction enzymes; and said digesting step is separately performed with each of said frequent cutter restriction enzymes.

4. The method of claim 1, wherein said frequent cutter restriction enzyme is one or both of Dpn II or NlaIII.

5. The method according to claim 1, wherein said amplifying step comprises the use of a G+C enhancing agent.

6. The method according to claim 5, wherein said G+C amplifying agent is tetramethylene sulfoxide (TMS).

* * * * *